(12) United States Patent
Bittar et al.

(10) Patent No.: US 10,338,030 B2
(45) Date of Patent: Jul. 2, 2019

(54) DEFECTS INSPECTION THROUGH DETECTION OF MAGNETIC FIELDS

(71) Applicant: Halliburton Energy Services, Inc., Houston, TX (US)

(72) Inventors: Michael S. Bittar, Houston, TX (US); Jing Li, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 95 days.

(21) Appl. No.: 14/647,561

(22) PCT Filed: Dec. 31, 2012

(86) PCT No.: PCT/US2012/072300
§ 371 (c)(1),
(2) Date: May 27, 2015

(87) PCT Pub. No.: WO2014/105080
PCT Pub. Date: Jul. 3, 2014

(65) Prior Publication Data
US 2015/0308980 A1    Oct. 29, 2015

(51) Int. Cl.
*E21B 47/00* (2012.01)
*E21B 47/08* (2012.01)
(Continued)

(52) U.S. Cl.
CPC ............ *G01N 27/82* (2013.01); *E21B 47/00* (2013.01); *E21B 47/082* (2013.01); *E21B 47/0905* (2013.01); *G01N 27/902* (2013.01)

(58) Field of Classification Search
CPC .... E21B 47/00; E21B 47/082; E21B 47/0905; G01N 27/82; G01N 27/902; G01N 27/83; G01N 27/87; G01R 15/202; G01R 15/148
(Continued)

(56) References Cited

U.S. PATENT DOCUMENTS 1,934,079 A * 11/1933 Lundberg ................. G01V 3/02
324/358
2,049,764 A * 8/1936 Drake ..................... G01N 27/83
324/260

(Continued)

FOREIGN PATENT DOCUMENTS

EP         0825435  A1    2/1998
WO   WO-2006/099133 A1   9/2006
(Continued)

OTHER PUBLICATIONS

Mercotac, Service Instructions, Sep. 2009.*
(Continued)

*Primary Examiner* — Justin Seo
*Assistant Examiner* — David L Singer
(74) *Attorney, Agent, or Firm* — Gilliam IP PLLC

(57) ABSTRACT

Various embodiments include apparatus and methods to inspect casing defects in a pipe such as a casing associated with a drilling operation. Electrical connectors contacting the inside wall of the pipe can be used to generate a current in the pipe. Magnetic fields correlated to an anomaly or anomalies that alter the current can be sensed to identify the presence of the anomaly or anomalies. Additional apparatus, systems, and methods are disclosed.

26 Claims, 7 Drawing Sheets

(51) Int. Cl.
*E21B 47/09* (2012.01)
*G01N 27/82* (2006.01)
*G01N 27/90* (2006.01)

(58) Field of Classification Search
USPC ..... 73/152.54; 324/221, 263, 220, 357, 359, 324/355–356, 360–361
See application file for complete search history.

(56) References Cited

U.S. PATENT DOCUMENTS

| | | | | |
|---|---|---|---|---|
| 2,099,823 A * | 11/1937 | Perry | G01N 27/83 | 324/217 |
| 2,108,463 A * | 2/1938 | Zuschlag | G01V 3/06 | 324/359 |
| 2,414,194 A * | 1/1947 | Ennis | G01V 3/22 | 324/355 |
| 2,669,688 A * | 2/1954 | Doll | G01V 3/20 | 174/113 R |
| 2,965,838 A * | 12/1960 | Kister | G01V 3/24 | 324/367 |
| 2,980,854 A * | 4/1961 | En Dean | C23F 13/04 | 324/351 |
| 3,105,191 A * | 9/1963 | Schopper | G01V 3/20 | 324/374 |
| 3,363,170 A * | 1/1968 | Gieske | E21B 47/082 | 324/221 |
| 3,539,915 A * | 11/1970 | Wood | G01N 27/904 | 324/220 |
| 3,555,412 A * | 1/1971 | Fowler | G01N 27/83 | 324/228 |
| 3,568,053 A * | 3/1971 | Kilpatrick | E21B 17/1021 | 324/325 |
| 3,593,122 A | 7/1971 | Barton et al. | | |
| 3,895,289 A * | 7/1975 | Rickey | G01V 3/24 | 324/323 |
| 4,015,195 A * | 3/1977 | Hoyer | G01V 3/24 | 324/323 |
| 4,087,749 A * | 5/1978 | McCormack | G01R 33/07 | 324/225 |
| 4,107,598 A | 8/1978 | Meador et al. | | |
| 4,292,589 A * | 9/1981 | Bonner | E21B 47/082 | 324/221 |
| 4,372,398 A * | 2/1983 | Kuckes | E21B 47/02 | 166/66.5 |
| 4,510,447 A | 4/1985 | Moyer | | |
| 4,609,873 A | 9/1986 | Cox et al. | | |
| 4,675,604 A * | 6/1987 | Moyer | G01N 27/82 | 324/220 |
| 4,794,322 A * | 12/1988 | Davies | E21B 41/02 | 324/347 |
| 5,230,387 A * | 7/1993 | Waters | E21B 7/068 | 175/45 |
| 5,397,985 A * | 3/1995 | Kennedy | E21B 47/0002 | 324/221 |
| 5,454,276 A * | 10/1995 | Wernicke | G01N 27/9013 | 324/220 |
| 5,479,100 A * | 12/1995 | Fowler | G01N 27/82 | 324/220 |
| 5,537,035 A * | 7/1996 | Fowler | G01N 27/82 | 324/220 |
| 5,581,037 A | 12/1996 | Kwun et al. | | |
| 6,037,767 A * | 3/2000 | Crescenzo | G01N 27/82 | 324/220 |
| 6,232,773 B1 | 5/2001 | Jacobs et al. | | |
| 6,538,437 B2 | 3/2003 | Spitzer et al. | | |
| 6,847,207 B1 * | 1/2005 | Veach | F16L 55/26 | 324/220 |
| 6,888,359 B2 * | 5/2005 | Hands | G01N 17/02 | 324/700 |
| 7,095,223 B2 | 8/2006 | Yoo | | |
| 7,795,864 B2 | 9/2010 | Barolak et al. | | |
| 2003/0201771 A1 * | 10/2003 | Krivoi | G01N 27/83 | 324/263 |
| 2005/0285588 A1 * | 12/2005 | Katragadda | B61K 9/10 | 324/126 |
| 2006/0164091 A1 | 7/2006 | Nestleroth et al. | | |
| 2008/0276731 A1 * | 11/2008 | Fagbayi | C23F 13/04 | 73/865.8 |
| 2011/0167914 A1 * | 7/2011 | Sutherland | F17D 1/00 | 73/643 |
| 2011/0308859 A1 | 12/2011 | Bittar et al. | | |
| 2011/0309836 A1 * | 12/2011 | Bittar | G01V 3/26 | 324/339 |
| 2014/0200831 A1 * | 7/2014 | Smith | G01M 5/0025 | 702/38 |

FOREIGN PATENT DOCUMENTS

WO WO-2010/013047 A1 2/2010
WO WO-2014105080 A1 7/2014

OTHER PUBLICATIONS

Mercotac, Model 110, 2011.*
"European Application Serial No. 12891260.7, Extended European Search Report dated May 30, 2016", 6 pgs.
"European Application Serial No. 12891260.7, Official Action dated Jul. 21, 2015", 2 pgs.
"European Application Serial No. 12891260.7, Reply filed Jan. 21, 2016 to Official Action dated Jul. 21, 2015", 8 pgs.
"International Application Serial No. PCT/US2012/072300, International Preliminary Report on Patentability dated Apr. 9, 2015", 10 pgs.
"International Application Serial No. PCT/US2012/072300, International Search Report dated Sep. 24, 2013", 3 pgs.
"International Application Serial No. PCT/US2012/072300, Written Opinion dated Sep. 24, 2013", 9 pgs.
"Gulf Cooperation Council Application Serial No. 2013-26180, First Examiner Report dated Nov. 17, 2016", 4 pages.
Mexican Application Serial No. MX/a/2015/008160; Office Action: dated Jan. 16, 2019, 6 pages, including English tanslation.

* cited by examiner

DEFECTS INSPECTION THROUGH DETECTION OF MAGNETIC FIELDS

PRIORITY APPLICATIONS

This application is a U.S. National Stage Filing under 35 U.S.C. 371 from International Application No. PCT/US2012/072300, filed on 31 Dec. 2012, which application is incorporated herein by reference in its entirety.

TECHNICAL FIELD

The present invention relates generally to apparatus for making measurements related to oil and gas exploration.

BACKGROUND

In drilling wells for oil and gas exploration, understanding the structure and properties of the associated geological formation provides information to aid such exploration. Measurements in a borehole are typically performed to attain this understanding. However, the pressure and temperatures accompanying measurement tools in the borehole of a well can affect operation of these tools in the borehole.

Various tools have been utilized to detect anomalies in casings associated with a drilling operation. For example, U.S. Pat. No. 7,795,864 B2 employs permanent magnets to generate magnetic flux in the casing such that, when the magnetic flux encounters an anomaly, the magnetic field will change directions in a nearby region. A Hall sensor can detect the change of the magnetic field such that signals from detecting the change can be processed to obtain anomaly information. WO 2010/013047 (PCT/GB/2009/050940) uses a coil antenna to induce eddy current in a casing and obtain the casing property by measuring the eddy current phase and strength. The usefulness of such measurements may be related to the precision or quality of the information derived from such measurements.

DETAILED DESCRIPTION

The following detailed description refers to the accompanying drawings that show, by way of illustration and not limitation, various embodiments in which the invention may be practiced. These embodiments are described in sufficient detail to enable those skilled in the art to practice these and other embodiments. Other embodiments may be utilized, and structural, logical, and electrical changes may be made to these embodiments. The various embodiments are not necessarily mutually exclusive, as some embodiments can be combined with one or more other embodiments to form new embodiments. The following detailed description is, therefore, not to be taken in a limiting sense.

In various embodiments, a tool can be arranged to detect anomalies in a pipe such as a metal casing associated with a drilling operation. The tool can include two electric connectors and at least one magnetic sensor. The two electric connectors can be structured to contact the casing from inside the casing with these electrical connectors at a specified distance from each other to excite an alternating current in the casing flowing in the longitudinal direction of the casing. The magnetic sensor can be arranged to pick up (detect) the magnetic field at the site of interest. When the current flow confronts any anomalies in the casing, a magnetic field other than the background field is generated. The tool can receive the induced magnetic field at its magnetic sensor or sensors, where the received induced magnetic field provides a signal(s) that can be processed to obtain the exact location and size of the anomaly. The anomaly can be corrosion (loss of material or cracks).

Figure 1:
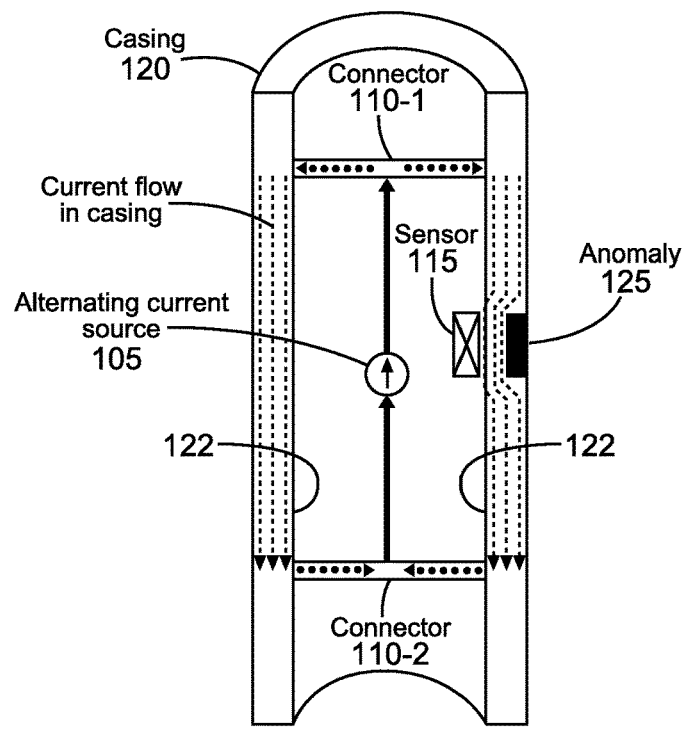
FIG. 1 shows an example architecture to detect anomalies in a conductive pipe associated with a drilling operation, in accordance with various embodiments.

FIG. 1 shows an embodiment of an example architecture to detect anomalies in a conductive pipe such as a casing associated with a drilling operation. The architecture includes an alternating current source 105, two electric connectors 110-1 and 110-2, and at least one magnetic sensor 115. Examples of magnetic sensors include, but are not limited to, coils, magnetometers, Hall effect magnetic field sensors, and other sensors to receive magnetic signals. The connectors 110-1 and 110-2 are selected and arranged to maintain good electric connection with casing 120 while sliding or spiraling along wall 122 inside casing 120. Connectors 110-1 and 110-2 can be rings or electrodes. Magnetic sensor(s) 115 and connectors 110-1 and 110-2 can be located in the same housing or in different housings. In either case, magnetic sensor(s) 115 can be located inside casing 120 between the two connectors to sense change of current due to anomalies.

A current from alternating current source 105 can be applied through electric connectors 110-1 and 110-2 to form a current flow in casing 120. Once the current in casing 120 confronts any defect or anomaly 125, it will change flowing direction and generate magnetic fields. The shape and size of the anomalies can be obtained from picking up and processing the magnetic signals while sensor 115 scans over the anomalies. Electric connectors 110-1 and 110-2 with sensor 115 located between electric connectors 110-1 and 110-2 can scan over anomalies with the tool containing these elements being pulled through the pipe. The method of pulling the tool through the pipe may depend on the deployment method being implemented. For an example wireline deployment, the tool can be pulled or conveyed by pipe or cable. For an example logging-while-drilling (LWD) deployment, the tool can be pulled by drilling pipe. For an example pipeline inspection, the tool can be pulled by pipeline tractors or other means.

Connectors 110-1 and 110-2 are structured to keep in touch with casing 120 while sliding along inside casing 120. The connectors can be spring-driven or can be of spring type structures. Both types of connectors have the ability of maintaining good contact while sliding inside casing 120.

Figure 2:
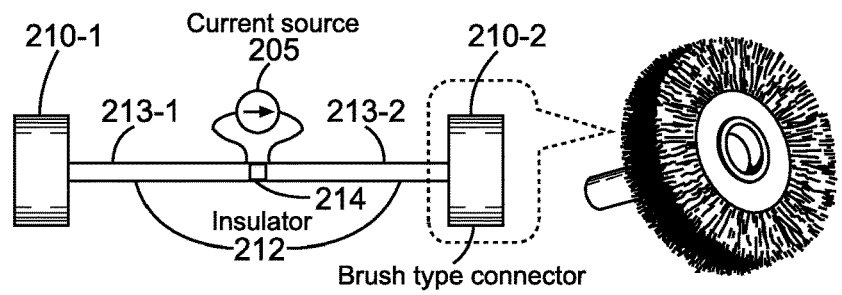
FIG. 2 shows example brush type connectors, in accordance with various embodiments.

FIG. 2 shows an example embodiment of example brush type connectors. The arrangement of the brush type connectors can include brush type electric connectors 210-1 and 210-2 coupled to a conductive structure 212 having a first conductive portion 213-1 separated from a second conductive portion 213-2 by an insulator 214. Conductive structure 212 can include copper, steel, or any conducting metal. Conductive structure 212 may have a rod-like structure. Other coupling structures can be used. For wireline deployment, conductive structure 212 may be a small conducting pipe. For LWD deployment, conductive structure 212 may use a drill collar with insulated cap or toroid. When disposed in a casing, conductive structure 212 can be located along the longitudinal axis of the casing with electric connectors 210-1 and 210-2 contacting the walls of the casing. The casing may be in a vertical position, a horizontal position, or at an angle from the vertical. With insulator 214 separating first conductive portion 213-1 from second conductive portion 213-2, first conductive portion 213-1 can be coupled to one contact of an alternating source 205 and second conductive portion 213-1 to another contact of alternating source 205. Insulator 214 can have a thickness of 1 to 3 inches to separate first conductive portion 213-1 from second conductive portion 213-2. Other separation distances can be used. This arrangement effectively allows alternating current source 205 to contact the casing or pipe via brush type electric connectors 210-1 and 210-2 to conduct current.

Figure 3:
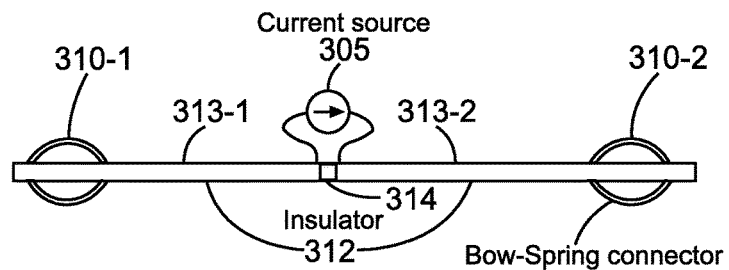
FIG. 3 illustrates example bow-spring connectors, in accordance with various embodiments.

FIG. 3 illustrates an example embodiment of example bow-spring connectors. The arrangement of the bow-spring connectors can include bow-spring electric connectors 310-1 and 310-2 coupled to a conductive structure 312 having a first conductive portion 313-1 separated from a second conductive portion 313-2 by an insulator 314. Conductive structure 312 can include copper, steel, or any conducting metal. Conductive structure 312 may have a rod-like structure. Other coupling structures can be used. For wireline deployment, conductive structure 312 may be a small conducting pipe. For LWD deployment, conductive structure 312 may use a drill collar with insulated cap or toroid. When disposed in a casing, conductive structure 312 can be located along the longitudinal axis of the casing with electric connectors 310-1 and 310-2 contacting the walls of the casing. The casing may be in a vertical position, a horizontal position, or at an angle from the vertical. With insulator 314 separating first conductive portion 313-1 from second conductive portion 313-2, first conductive portion 313-1 can be coupled to one contact of an alternating source 305 and second conductive portion 313-1 to another contact of alternating source 305. Insulator 314 can have a thickness of 1 to 3 inches to separate first conductive portion 313-1 from second conductive portion 313-2. Other separation distances can be used. This arrangement effectively allows alternating current source 305 to contact the casing or pipe via bow-spring electric connectors 310-1 and 310-2 to conduct current.

Figure 5:
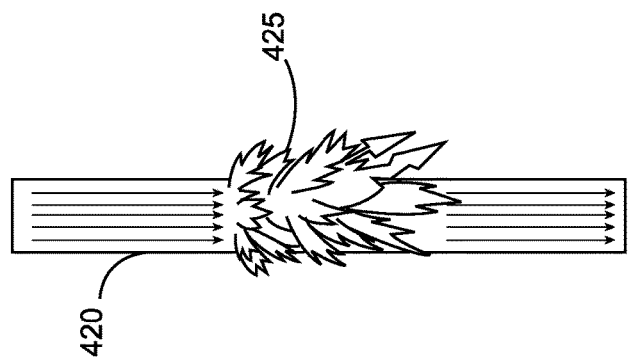
FIG. 5 shows a model of a current distribution in the casing of FIG. 4, in accordance with various embodiments.
Figure 4:
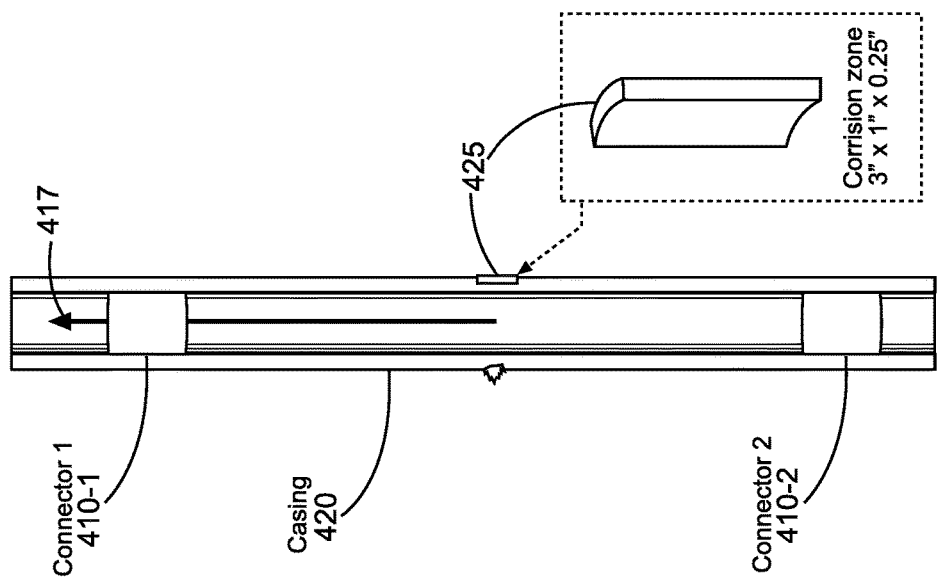
FIG. 4 shows a model configuration to inspect casing corrosion by current flux, in accordance with various embodiments.

FIG. 4 shows a model configuration to inspect casing corrosion by current flux. The model configuration shows a casing 420 having an anomaly 425, where two electric connectors 410-1 and 410-2 are employed to contact casing 420 from inside casing 420 and to apply an alternating current to casing 420. FIG. 5 shows a model of the current distribution in casing 420 within the zone between the two connectors 410-1 and 410-2 of FIG. 4. It can be seen that the current flows smoothly in the longitudinal direction 417 in casing 420 where no corrosion zone or anomaly is present in casing 420. However, the current changes direction when it confronts anomaly 425. Consequently, the secondary magnetic field generated by the current will vary.

Figure 6:
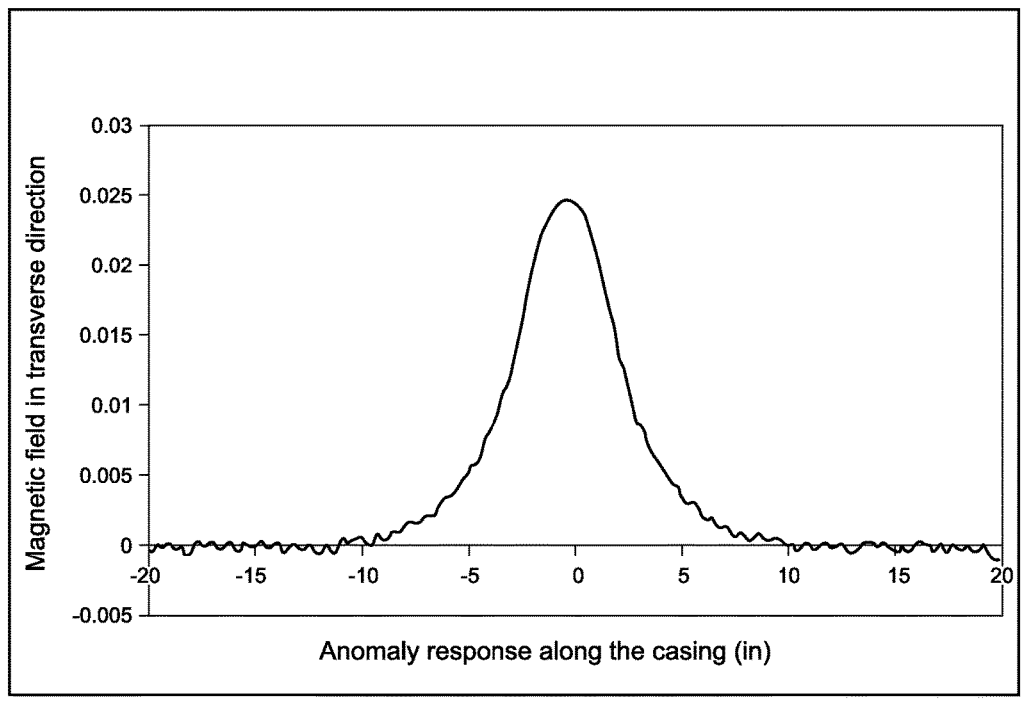
FIG. 6 shows a modeled transverse magnetic field induced by the anomaly in the casing of FIG. 4, in accordance with various embodiments.
Figure 7:
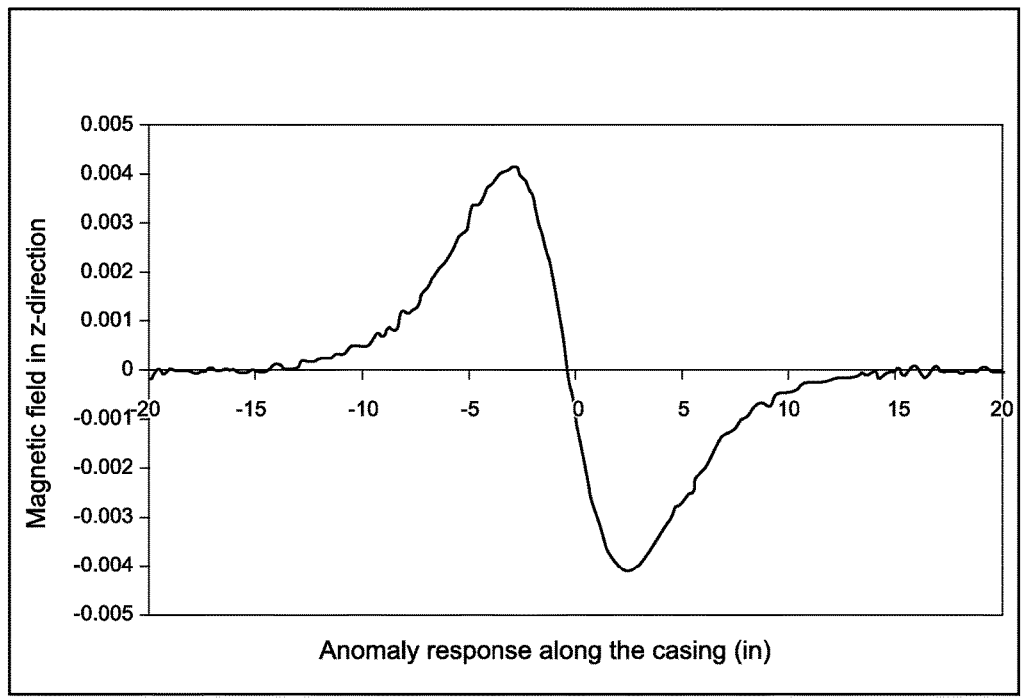
FIG. 7 shows a modeled longitudinal magnetic field induced by the anomaly in the casing of FIG. 4, in accordance with various embodiments.

FIGS. 6 and 7 show modeled anomaly response along casing 420 of FIG. 4. The modeling shows the magnetic field induced by the current as the transceivers move along a wall inside casing 420 along the longitudinal direction 417. FIG. 6 shows the transversely polarized field, and FIG. 7 shows the longitudinally polarized field. The corrosion zone or anomaly 225 has a size of 3"×1"×0.25" and is located at z=0. FIGS. 6 and 7 illustrate that the magnetic fields change significantly, when the sensor scans over the anomaly.

Figure 8:
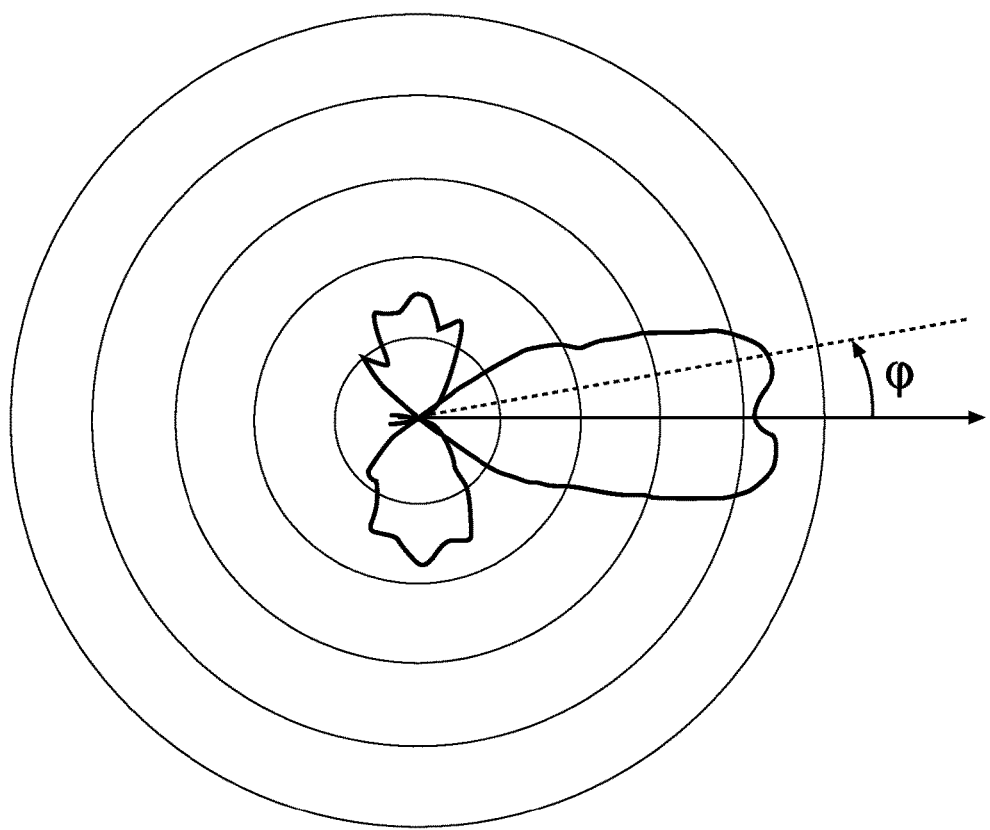
FIG. 8 shows a modeled anomaly response along the casing of FIG. 4 near the anomaly as a function of azimuthal angle, in accordance with various embodiments.

FIG. 8 shows a modeled anomaly response along casing 420 of FIG. 4 near anomaly 425 as a function of azimuthal angle. The modeled response shows the magnetic field near anomaly 425 varying with the azimuthal angle. When the sensor rotates 360 degree in azimuthal angles, the maximum signals are recorded at two edges of anomaly 425. The signal becomes very small when the sensor goes off the anomaly. For 360 degree coverage, the sensor can be rotated around the inside of the pipe or a number of sensors can be disposed to be located around the pipe between the two electrical connections to obtain 360 degree coverage. For example, the lumber of sensors may range from 4 to 32, 64, or other appropriate number.

The 360 degree coverage can provide signals to image the anomalies. In addition, the electrical connectors can be rotated as well as the sensor inside the pipe for contact and sensing for azimuthal 360 degree coverage. For wireline deployment, a motor that rotates the sensor or a motor that rotates both the sensor and the brushes or electrodes can be used. For LWD deployment, rotating the housing of the sensor and the brushes or electrodes can be conducted or rotating a collar, on which the sensor and the brushes or electrodes are mounted, can be conducted. The measurement can be continuous with the motor rotating relatively fast or can be made on a stationary basis.

Figure 9:
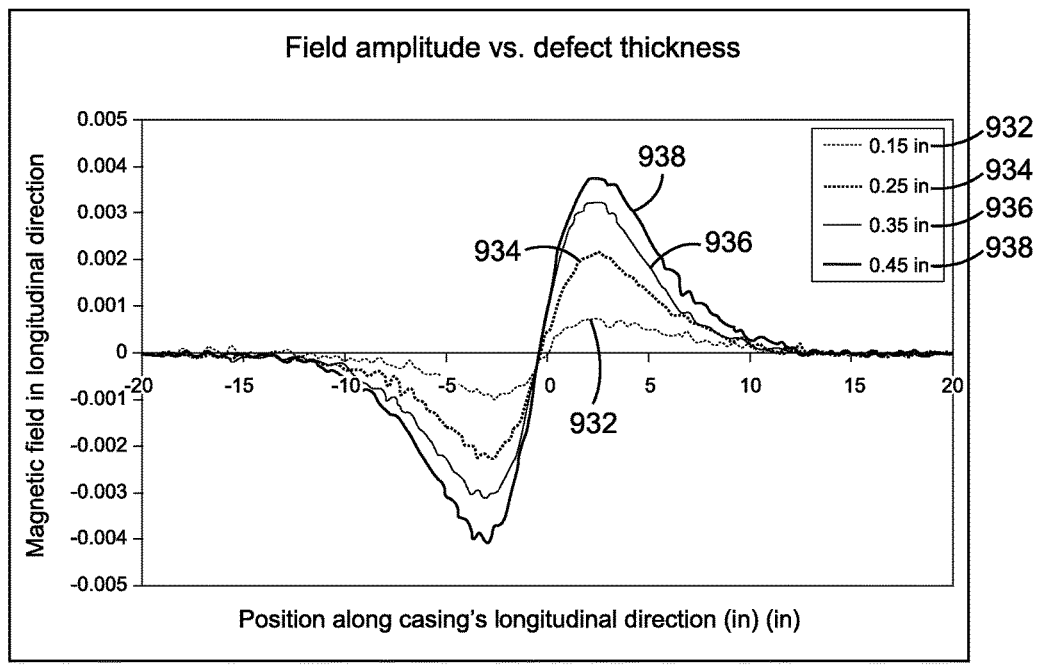
FIG. 9 shows a modeled magnetic field in a longitudinal direction with respect to defect thickness, in accordance with various embodiments.
Figure 10:
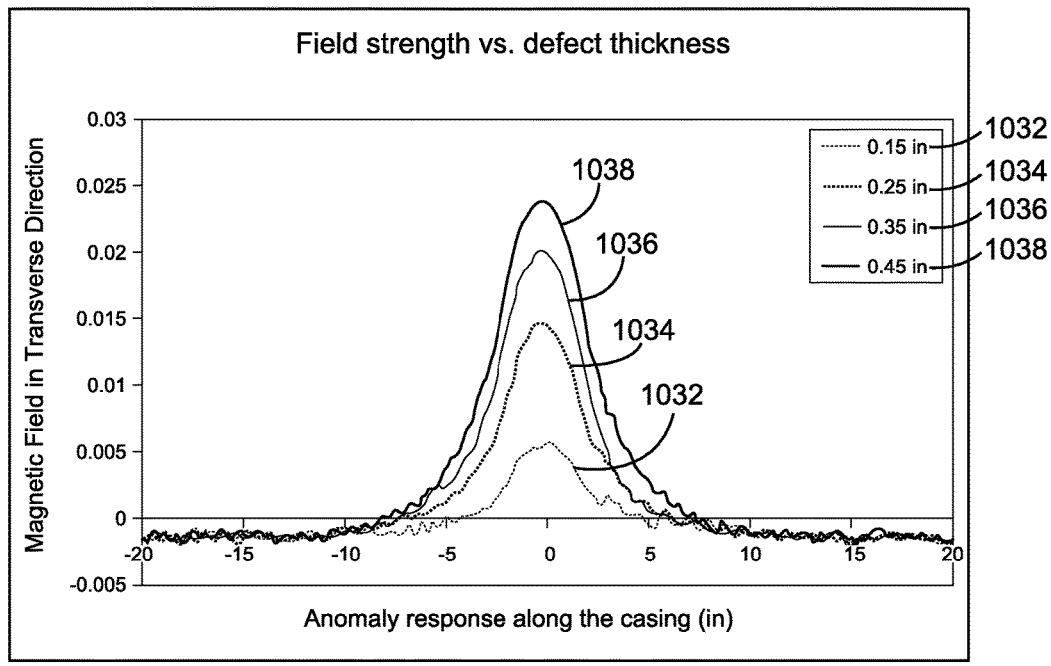
FIG. 10 shows a modeled magnetic field in a transverse direction with respect to defect thickness, in accordance with various embodiments.

FIGS. 9 and 10 show modeled responses of the anomaly with different thickness. The thicker the anomaly, the stronger signals are recorded. This correlation provides a reliable method to determine the anomaly thickness. Curves 932 and 1032 indicate a defect thickness of 0.15 inches. Curves 934 and 1034 indicate a defect thickness of 0.25 inches. Curves 936 and 1036 indicate a defect thickness of 0.35 inches. Curves 938 and 1038 indicate a defect thickness of 0.55 inches. Tables and/or plots similar to FIGS. 9 and 10 can be generated for the different types of material used in casings, or other conductive pipe, such that each measurement tool can be calibrated for the type of material. Based on the calibration, tables or figures similar to FIGS. 9 and 10 can be used to determine the thickness loss of material. When the anomaly is a crack, depending on the orientation of the crack, there may or may not be a current flow. Calibration for pipe material can be implemented to establish a baseline.

Anomaly thickness can be determined by strength of magnetic field and the established calibrated baseline for different materials.

Calibration procedures can be conducted to provide the three dimensional (3D) size of the anomaly. The tool can be rotated in pipe material where there is no anomaly to establish a baseline. The magnetic field strength can be mapped to thickness loss azimuthally and in the Z direction (longitudinal axis of the casing) as the tool is moved along the length of the casing. For 3D anomaly mapping, the sensor can be rotated 360 degree and corrosion loss can be calculated azimuthally and vertically.

A tool, including separated electrical connectors arranged with a sensor in manner similar to or identical to the tools disclosed herein, can be operable to apply electric current directly onto a casing. Using contacts to inject current in the casing pipe and not an induction coil avoids generation of primary magnetic fields near the sensor that would be a significant interference to the true signals. As a result, high signal-to-noise ratio can be obtained. Therefore, high accuracy of measurement and low cost in electric circuitry can be expected.

In various embodiments, features of an example method to inspect defects in a pipe can include: generating an alternating current in a wall of a pipe between two connectors contacting an inside of the wall, the two connectors coupled to a current source; moving the two connectors along the inside of the wall; and determining if an anomaly exists in the pipe as the two connectors move along the inside wall by detecting a magnetic field in a magnetic sensor when scanning over the anomaly, the magnetic field indicative of the anomaly. The two connectors can be operated to maintain contact along the inside wall of the pipe as the two connectors slide or spiral along the inside wall. The two connectors can be brush type connectors. The two connectors can be bow-spring connectors. The magnetic sensor can be a coil or a magnetometer. The method can include processing a signal from the magnetic field, generating a representation of the anomaly in shape, size, or a combination of shape and size. The method can include rotating the magnetic sensor around the inside of the pipe. The method can include determining thickness of the anomaly based on the strength of the magnetic field. The method can include displaying an image of the anomaly. The image may be displayed on a video screen, a print medium, or other structure to visually project information regarding the detected anomaly.

In various embodiments, components of a system operable to detect anomalies in a pipe, such as a casing associated with a drilling operation, as described herein or in a similar manner, can be realized in combinations of hardware and software based implementations. These implementations can include a machine-readable storage device having machine-executable instructions, such as a computer-readable storage device having computer-executable instructions, to detect anomalies in a pipe. Executed instructions can also include instructions to activate one or more electrodes to generate current in a pipe from a current source. Executed instructions can also include instructions to operate one or more magnetic sensors to provide signals in response to perturbations of the current generated from the electrodes through the pipe in accordance with the teachings herein. The instructions can include instructions to provide data to a data processing unit such that the data processing unit conducts one or more processes to evaluate signals, data, or signals and data. Further, a machine-readable storage device, herein, is a physical device that stores data represented by physical structure within the device. Examples of machine-readable storage devices include, but are not limited to, read only memory (ROM), random access memory (RAM), a magnetic disk storage device, an optical storage device, a flash memory, and other electronic, magnetic, and/or optical memory devices.

A machine-readable storage device having instructions stored thereon, which, when performed by a machine, cause the machine to perform operations, can comprise instructions to: collect data from magnetic sensors disposed in a tool in response to generating an alternating current in a wall of a pipe between two connectors of the tool contacting an inside of the wall, as the two connectors move along the inside of the wall; and determine, from the collected data, if an anomaly exists in the pipe as the two connectors move along the inside wall. The instructions can include instructions to: generate the alternating current from a current source coupled to the two connectors; and move the two connectors along the inside of the wall.

The instructions can include instructions to process the collected data and to generate a representation of the anomaly in shape, size, or a combination of shape and size. The instructions can include instructions to access a database having calibration data correlating characteristics of the anomaly to material of the pipe as a function of sensed magnetic field. The instructions can include instructions to determine thickness of the anomaly based on strength of a magnetic field represented in the collected data. The instructions can include instructions to display an image of the anomaly. The image may be displayed on a video screen, a print medium, or other structure to visually project information regarding the detected anomaly.

Figure 11:
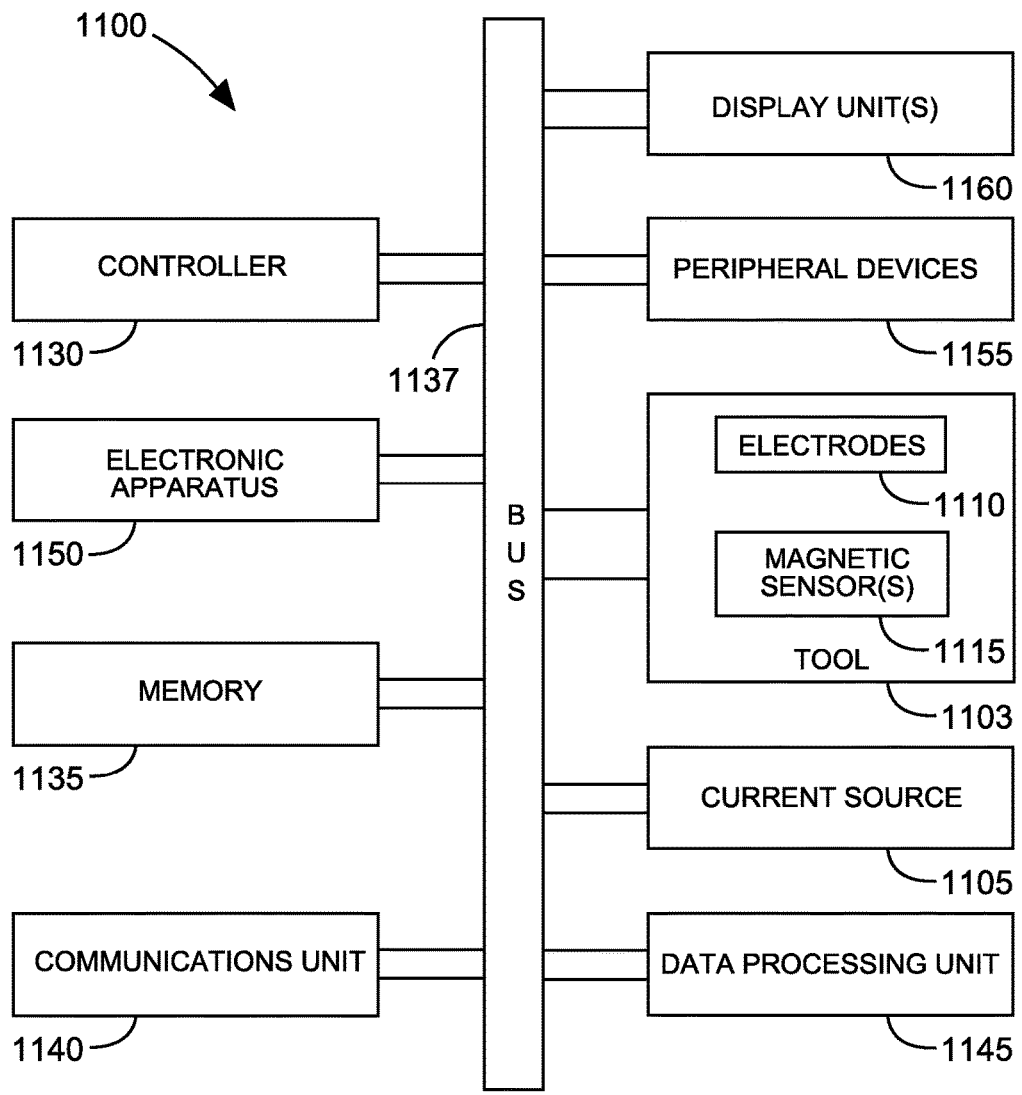
FIG. 11 depicts a block diagram of features of an example system having a tool to detect anomalies in a pipe, in accordance with various embodiments.

FIG. 11 depicts a block diagram of features of an example embodiment of a system 1100 having a tool 1103 operable to detect an anomaly in a pipe such as a casing associated with a drilling operation. Tool 1103 can include electrodes 1110 that provide current flow in the pipe from current source 1105, where perturbations to the current flow due to an anomaly in the pipe can be detected by one or more magnetic sensors 1115 of tool 1103. Electrodes 1110 can be structured as separated electrical connections that contact and maintain contact to the inside walls of the pipe as tool 1103 moves along the inside walls of the pipe. Magnetic sensor(s) 1115 of tool 1103 can be disposed between two of electrodes 1110. Current source 1105 can be integrated with tool 1103 or arranged separately with electrically leads to each of electrodes 1110. Tool 1103, electrodes 1110, magnetic sensor(s) 1115, and current source 1105 can be structured to operate downhole in a pipe and can be structured similar to or identical to a configuration associated with any of FIGS. 1-3, 9, 10, and 12.

System 1100 can include a controller 1130, a memory 1135, an electronic apparatus 1150, and a communications unit 1140. Controller 1130, memory 1135, and communications unit 1140 can be arranged to operate as a processing unit to control management of tool 1103 and to perform operations on data signals collected by tool 1103. Memory 1135 can include a database having calibration data correlating characteristics of an anomaly to material of the pipe as a function of magnetic field sensed by magnetic sensor(s) 1115 of tool 1103. A data processing unit can be distributed among the components of system 1100 including electronic apparatus 1150. Alternatively, system 1100 can include a data processing unit 1145 to manage data associated with tool 1103.

Communications unit 1140 can include downhole communications for communication to the surface at a well from tool 1103. Such downhole communications can include a telemetry system. Communications unit 1140 may use combinations of wired communication technologies and wireless technologies at frequencies that do not interfere with on-going measurements.

System 1100 can also include a bus 1137, where bus 1137 provides electrical conductivity among the components of system 1100. Bus 1137 can include an address bus, a data bus, and a control bus, each independently configured. Bus 1137 can be realized using a number of different communication mediums that allows for the distribution of components of system 1100. Use of bus 1137 can be regulated by controller 1130.

In various embodiments, peripheral devices 1155 can include additional storage memory and/or other control devices that may operate in conjunction with controller 1130 and/or memory 1135. In an embodiment, controller 1130 is realized as a processor or a group of processors that may operate independently depending on an assigned function. Display unit(s) 1160 can be arranged with a screen display, as a distributed component on the surface, that can be used with instructions stored in memory 1135 to implement a user interface to manage the operation of tool 1103 and/or components distributed within system 1100. Such a user interface can be operated in conjunction with communications unit 1140 and bus 1137. Display unit(s) 1160 can include a video screen, a printing device, or other structure to visually project information regarding the detected anomaly. The presented data can include data regarding the presence or absence of an anomaly in a pipe examined using tool 1103.

Figure 12:
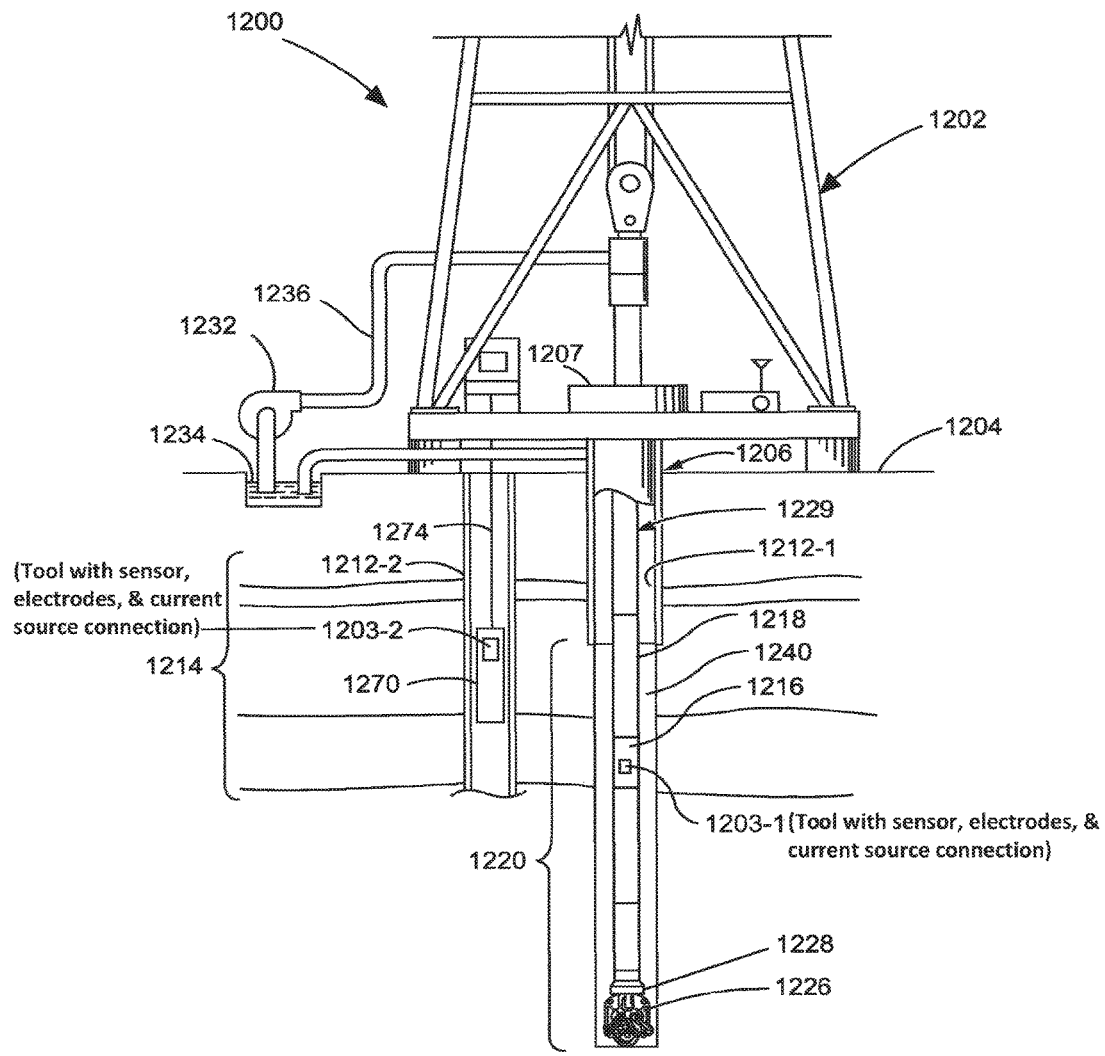
FIG. 12 depicts an example system at a drilling site, where the system includes a tool to detect anomalies in a pipe, in accordance with various embodiments.

FIG. 12 depicts an embodiment of a system 1200 at a drilling site, where the system 1200 can include a tool 1203-1, 1203-2, or both 1203-1 and 1203-2 to detect anomalies in a pipe in which tool 1203-1 or 1203-2 is placed. Each of tools 1203-1 and 1203-2 include electrodes, structured as separated electrical connections that contact and maintain contact to the inside walls of the pipe being investigated as tool 1203-1 or 1203-2 moves along the inside walls of the pipe, where the electrodes provide current flow in the pipe from a current source such that perturbations to the current flow due to an anomaly in the pipe can be detected by one or more magnetic sensors of tools 1203-1 and 1203-2, respectively. Tools 1203-1 and 1203-2 can be realized in a similar or identical manner to arrangements taught herein to detect anomalies in a pipe.

System 1200 can include a drilling rig 1202 located at a surface 1204 of a well 1206 and a string of drill pipes, that is, drill string 1229, connected together so as to form a drilling string that is lowered through a rotary table 1207 into a wellbore or borehole 1212-1. Drilling rig 1202 can provide support for drill string 1229. Drill string 1229 can operate to penetrate rotary table 1207 for drilling the borehole 1212-1 through subsurface formations 1214. Drill string 1229 can include drill pipe 1218 and a bottom hole assembly 1220 located at the lower portion of drill pipe 1218.

The bottom hole assembly 1220 can include a drill collar 1216 and a drill bit 1226. Drill bit 1226 can operate to create borehole 1212-1 by penetrating the surface 1204 and the subsurface formations 1214. Bottom hole assembly 1220 can include tool 1203-1 attached to drill collar 1216 to be moved along the inside walls of a pipe, such as a casing, underground to detect anomalies in the pipe. Tool 1203-1 can be structured for an implementation in a measure-while-drilling (MWD) system such as a LWD system. The housing containing tool 1203-1 can include electronics to activate generation of current through electrodes of tool 1203-1 into a pipe being analyzed with respect to anomalies and collect responses from magnetic sensor(s) of tool 1203-1. Such electronics can include a processing unit to provide analysis of characteristics of detected anomalies to the surface over a standard communication mechanism for operating in a well. Alternatively, electronics can include a communications interface to provide signals output by magnetic sensor(s) of tool 1203-1 to the surface over a standard communication mechanism for operating in a well, where these output signals can be analyzed at a processing unit at the surface to determine characteristics of detected anomalies.

During drilling operations, drill string 1229 can be rotated by rotary table 1207. In addition to, or alternatively, the bottom hole assembly 1220 can also be rotated by a motor 1228 (e.g., a mud motor) that is located downhole. Drill collars 1216 can be used to add weight to drill bit 1226. Drill collars 1216 also can stiffen the bottom hole assembly 1220 to allow the bottom hole assembly 1220 to transfer the added weight to drill bit 1226, and in turn, assist drill bit 1226 in penetrating surface 1204 and subsurface formations 1214. This apparatus or similar apparatus can be used to move, rotate, and otherwise control motion of tool 1203-1 within a pipe.

During drilling operations, a mud pump 1232 can pump drilling fluid (sometimes known by those of skill in the art as "drilling mud") from a mud pit 1234 through a hose 1236 into drill pipe 1218 and down to drill bit 1226. The drilling fluid can flow out from drill bit 1226 and be returned to the surface 1204 through an annular area 1240 between drill pipe 1218 and the sides of the borehole 1212-1. The drilling fluid may then be returned to mud pit 1234, where such fluid is filtered. In some embodiments, the drilling fluid can be used to cool drill bit 1226, as well as to provide lubrication for drill bit 1226 during drilling operations. Additionally, the drilling fluid may be used to remove subsurface formation 1214 cuttings created by operating drill bit 1226.

In various embodiments, tool 1203-2 may be included in a tool body 1270 coupled to a logging cable 1274 such as, for example, for wireline applications. The tool body 1270 containing the tool 1203-2 can include electronics to activate generation of current through electrodes of tool 1203-2 into a pipe being analyzed with respect to anomalies and collect responses from magnetic sensor(s) of tool 1203-2. Such electronics can include a processing unit to provide analysis of characteristics of detected anomalies to the surface over a standard communication mechanism for operating in a well. Alternatively, electronics can include a communications interface to provide signals output by magnetic sensor(s) of tool 1203-2 to the surface over a standard communication mechanism for operating in a well, where these output signals can be analyzed at a processing unit at the surface to determine characteristics of detected anomalies. The logging cable 1274 may be realized as a wireline (multiple power and communication lines), a mono-cable (a single conductor), and/or a slick-line (no conductors for power or communications), or other appropriate structure for use in the borehole 1212-2. This apparatus or similar apparatus can be used to move, rotate, and otherwise control motion of tool 1203-2 within a pipe.

Although specific embodiments have been illustrated and described herein, it will be appreciated by those of ordinary skill in the art that any arrangement that is calculated to achieve the same purpose may be substituted for the specific embodiments shown. Various embodiments use permutations and/or combinations of embodiments described herein. It is to be understood that the above description is intended to be illustrative, and not restrictive, and that the phraseology or terminology employed herein is for the purpose of description. Combinations of the above embodiments and other embodiments will be apparent to those of skill in the art upon studying the above description.

What is claimed is:

1. An apparatus comprising:
    two electric connectors coupled to an alternating current source and contacting an inside wall of a pipe of a given material to flow a current into the pipe from the alternating current source between the two electric connectors, wherein the pipe is located downhole in a formation;
    a magnetic sensor positioned between the two electric connectors and operable to receive a magnetic field in response to flowing the current while the magnetic sensor scans over the inside wall of the pipe, wherein the scanning includes moving the magnetic sensor azimuthally around the inside wall of the pipe and longitudinally along the inside wall of the pipe;
    a processing unit operable to process the magnetic field to detect that a defect is located at a given azimuth and a given longitudinal position of the pipe and has a defect thickness, wherein the detection is based on: (i) a maximum strength of the magnetic field in a transverse direction to a longitudinal axis direction of the pipe; (ii) a maximum strength of the magnetic field in the longitudinal axis direction of the pipe; and (iii) calibration data for the given type material which correlates the maximum strength of the magnetic field in the transverse and longitudinal axis direction to the defect thickness.

2. The apparatus of claim 1, wherein the two electric connectors maintain contact along an inside wall of the pipe as the two electric connectors slide or spiral along the inside wall.

3. The apparatus of claim 1, wherein the two electric connectors are brush type connectors.

4. The apparatus of claim 1, wherein the two electric connectors are bow-spring connectors.

5. The apparatus of claim 1, wherein the apparatus includes the processing unit operable to process the magnetic field and to generate a representation of an anomaly in the pipe.

6. The apparatus of claim 5, wherein the representation includes a representation of shape, size, or a combination of shape and size.

7. The apparatus of claim 1, wherein the magnetic sensor is a coil or a magnetometer.

8. The apparatus of claim 1, wherein the magnetic sensor is operable to rotate and detect azimuth angles indicating edges of a detected anomaly.

9. The apparatus of claim 1, wherein the two electric connectors contacting the inside wall of the pipe are coupled to respective conductors, wherein the respective conductors are insulated from each other by an insulator and coupled to the alternating current source, wherein the insulator and respective conductors are linearly arranged to span in between the two electric connectors, and wherein the respective conductors comprise a metal tubular.

10. The apparatus of claim 1, further comprising a drill collar of a drill string and a tool attached to the drill collar, wherein the two electrical connectors are coupled to the drill collar of the drill string to flow the current around a circumference of the wall of the pipe, wherein the tool includes the magnetic sensor.

11. The apparatus of claim 1, further comprising a motor that rotates one or more of the magnetic sensor and the two electric connectors inside the pipe to flow the current around a circumference of the wall of the pipe.

12. A method comprising:
    generating an alternating current in a wall of a pipe of a given material between two connectors contacting an inside of the wall, the two connectors coupled to a current source, wherein the pipe is located downhole in a formation;
    moving the two connectors along the inside of the wall; and
    determining that an anomaly exists in the pipe as the two connectors move along the inside of the wall by detecting a magnetic field in a magnetic sensor when scanning over the anomaly, the magnetic field indicative of the anomaly, wherein the scanning includes moving the magnetic sensor azimuthally around the inside wall of the pipe and longitudinally along the inside wall of the pipe;
    wherein determining the anomaly comprises detecting that a defect is located at a given azimuth and a given longitudinal position of the pipe and has a defect thickness, wherein the detection is based on: (i) a maximum strength of the magnetic field in a transverse direction to a longitudinal axis direction of the pipe; (ii) a maximum strength of the magnetic field in the longitudinal axis direction of the pipe; and (iii) calibration data for the given type material which correlates the maximum strength of the magnetic field in the transverse and longitudinal axis direction to the defect thickness.

13. The method of claim 12, wherein the two connectors maintain contact along the inside of the wall of the pipe as the two connectors slide or spiral along the inside of the wall.

14. The method of claim 12, wherein the two connectors are brush type connectors.

15. The method of claim 12, wherein the two connectors are bow-spring connectors.

16. The method of claim 12, wherein the method includes processing a signal from the detected magnetic field, generating a representation of the anomaly in shape, size, or a combination of shape and size.

17. The method of claim 12, wherein the method includes rotating the magnetic sensor around the inside of the pipe.

18. The method of claim 12, wherein the magnetic sensor is a coil or a magnetometer.

19. The method of claim 12, wherein the method includes, based on determining that the anomaly exists, rotating the magnetic sensor to detect azimuth angles indicating edges of the anomaly.

20. The method of claim 12, wherein the two electric connectors contacting the inside wall of the pipe are coupled to respective conductors, wherein the respective conductors are insulated from each other by an insulator and coupled to the alternating current source wherein the insulator and respective conductors are linearly arranged to span in between the two electric connectors, and wherein the respective conductors comprise a metal tubular.

21. The method of claim 12, wherein moving the two connectors and the magnetic sensor comprises rotating a drill collar of a drill string which is coupled to the two connectors contacting the inside of the pipe, wherein the rotation causes the two connectors to rotate along the inside of the wall of the pipe to flow the current around a circumference of the wall of the pipe, wherein a tool is attached to the drill collar and wherein the tool includes the magnetic sensor.

22. The method of claim 12, wherein a motor is coupled to the two connectors in the pipe; and wherein moving the two connectors comprises rotating the two connectors along the inside of the wall via the motor to flow the current around a circumference of the wall of the pipe.

23. A system comprising:
a pipe of a given material, the pipe positioned downhole in a well of a subsurface formation;
a housing positioned inside the pipe, the housing comprising an alternating current source, two electric connectors coupled to the alternating current source; and a magnetic sensor positioned between the two electric connectors; and
machine-readable storage device having instructions stored thereon, which, when performed by a machine, cause the machine to perform operations, the instructions comprising instructions to:
move the two electric connectors along the inside of a wall of the pipe, wherein the two electric connectors are in substantially continuous contact with the inside surface of the wall;
generate alternating current in a portion of the wall between the two connectors;
collect data from the magnetic sensor in response to the generated alternating current, wherein the collecting includes moving the magnetic sensor azimuthally around the inside wall of the pipe and longitudinally along the inside wall of the pipe; and
determine, from the collected data, if an anomaly exists in the pipe as the two electric connectors move along the inside of the wall;
wherein determining if an anomaly exists comprises detecting if a defect is located at a given azimuth and a given longitudinal position of the pipe and has a defect thickness, wherein the detection is based on: (i) a maximum strength of the magnetic field in a transverse direction to a longitudinal axis direction of the pipe; (ii) a maximum strength of the magnetic field in the longitudinal axis direction of the pipe; and (iii) calibration data for the given type material which correlates the maximum strength of the magnetic field in the transverse and longitudinal axis direction to the defect thickness.

24. The system of claim 23, wherein the instructions include instructions to:
process the collected data and to generate a representation of the anomaly in shape, size, or a combination of shape and size; and
display an image of the anomaly.

25. The system of claim 23, wherein the instructions include instructions to determine, from the collected data, a first azimuth angle and a second azimuth angle indicating edges of a detected anomaly.

26. The system of claim 23, wherein the two electric connectors contacting the inside wall of the pipe are coupled to respective conductors, wherein the respective conductors are insulated from each other by an insulator and coupled to the alternating current source, wherein the insulator and respective conductors are linearly arranged to span in between the two electric connectors, and wherein the respective conductors comprise a metal tubular.

* * * * *